(12) United States Patent
Darling, IV et al.

(10) Patent No.: US 12,096,937 B2
(45) Date of Patent: Sep. 24, 2024

(54) SKIN CLOSURE DEVICES

(71) Applicant: DQ Holdings, LLC, Houston, TX (US)

(72) Inventors: Charles M. Darling, IV, Houston, TX (US); J. Rick Stockton, San Antonio, TX (US); Catherine M. Fonfara, Houston, TX (US); Charles M. Darling, V, Houston, TX (US); Christopher B. Darling, New York, NY (US)

( * ) Notice: Subject to any disclaimer, the term of this patent is extended or adjusted under 35 U.S.C. 154(b) by 335 days.

(21) Appl. No.: 16/814,681

(22) Filed: Mar. 10, 2020

(65) Prior Publication Data

US 2020/0337705 A1    Oct. 29, 2020

Related U.S. Application Data (60) Provisional application No. 62/838,623, filed on Apr. 25, 2019.

(51) Int. Cl.
*A61B 17/08* (2006.01)
*A61B 17/00* (2006.01)

(52) U.S. Cl.
CPC .......... *A61B 17/085* (2013.01); *A61B 17/083* (2013.01); *A61B 2017/00424* (2013.01); *A61B 2017/081* (2013.01)

(58) Field of Classification Search
CPC . A61B 17/085; A61B 17/08; A61B 2017/086; A61B 2017/088; A61B 2017/081
See application file for complete search history.

(56) References Cited

U.S. PATENT DOCUMENTS

| | | | |
|---|---|---|---|
| 1,774,489 A | 8/1930 | Sarason | |
| 2,196,286 A | 4/1940 | Barsky | |
| 3,068,869 A * | 12/1962 | Sheiden | A61B 17/08 606/221 |
| 3,288,137 A | 11/1966 | Lund | |
| 3,487,836 A | 1/1970 | Niebel | |
| 3,863,640 A | 2/1975 | Haverstock | |
| 3,926,193 A | 12/1975 | Hasson | |
| 3,971,384 A | 7/1976 | Hasson | |
| 3,983,878 A | 10/1976 | Kawchitch | |
| 4,114,624 A | 9/1978 | Haverstock | |
| 4,141,363 A | 2/1979 | James et al. | |
| 4,423,731 A | 1/1984 | Roomi | |
| 4,467,805 A | 8/1984 | Fukuda | |

(Continued)

FOREIGN PATENT DOCUMENTS

| | | |
|---|---|---|
| CN | 1635852 | 7/2005 |
| CN | 101229071 | 7/2008 |

(Continued)

OTHER PUBLICATIONS

PCT Search Report and Written Opinion for PCT App. No. PCT/US20/29360 Dated Sep. 2, 2020.

*Primary Examiner* — Katherine H Schwiker
(74) *Attorney, Agent, or Firm* — Remenick PLLC (57) ABSTRACT

Wound closure devices and methods of using the wound closure devices are disclosed. The wound closure device comprises two clips. Each clip comprises a wedge-shaped body, a tab extending from a tip of the wedge-shaped body, an anchor extending from a base of the wedge-shaped body, and a locking mechanism positioned within the wedge-shaped body.

17 Claims, 10 Drawing Sheets

(56) References Cited

U.S. PATENT DOCUMENTS

| | | |
|---|---|---|
| 4,526,173 A | 7/1985 | Sheehan |
| 4,535,772 A | 8/1985 | Sheehan |
| 4,539,990 A | 9/1985 | Stivala |
| 4,605,005 A | 8/1986 | Sheehan |
| 4,702,251 A | 10/1987 | Sheehan |
| 4,815,468 A | 3/1989 | Annand |
| 5,159,728 A | 11/1992 | Bingold |
| 5,176,703 A | 1/1993 | Peterson |
| 5,259,835 A | 11/1993 | Clark et al. |
| 5,263,973 A | 11/1993 | Cook |
| 5,486,196 A | 1/1996 | Hirshowitz et al. |
| 5,562,705 A | 10/1996 | Whiteford |
| 5,571,138 A | 11/1996 | Blomqvist et al. |
| 5,733,305 A | 3/1998 | Fleischmann |
| 5,843,123 A | 12/1998 | Brazeau |
| 6,010,524 A | 1/2000 | Fleischmann |
| 6,022,351 A | 2/2000 | Bremer et al. |
| 6,106,544 A | 8/2000 | Brazeau |
| 6,152,874 A | 11/2000 | Looney et al. |
| 6,176,868 B1 | 1/2001 | Detour |
| 6,329,564 B1 | 12/2001 | Lebner |
| 6,559,350 B1 | 5/2003 | Tetreault et al. |
| 6,596,917 B2 | 7/2003 | Oyaski |
| 7,361,185 B2 | 4/2008 | O'Malley et al. |
| 7,429,265 B2 | 9/2008 | O'Malley et al. |
| 8,157,839 B2 | 4/2012 | Riskin et al. |
| 8,313,508 B2 | 11/2012 | Belson et al. |
| 8,323,313 B1 | 12/2012 | Belson et al. |
| 8,336,463 B2 | 12/2012 | Smith |
| 8,439,945 B2 | 5/2013 | Belson et al. |
| 8,858,430 B2 | 10/2014 | Oyadiran et al. |
| 9,028,529 B2 | 5/2015 | Fox et al. |
| 9,050,086 B2 | 6/2015 | Belson et al. |
| 9,089,328 B2 | 7/2015 | Belson et al. |
| 9,179,914 B2 | 11/2015 | Belson et al. |
| 9,301,760 B2 | 4/2016 | Fox |
| 9,603,596 B2 | 3/2017 | Riskin et al. |
| 2002/0019649 A1 | 2/2002 | Sikora et al. |
| 2005/0033215 A1 | 2/2005 | Lebner |
| 2005/0070927 A1 | 3/2005 | Feinberg |
| 2009/0036922 A1 | 2/2009 | Riskin et al. |
| 2009/0177227 A1 | 7/2009 | Warren |
| 2011/0022082 A1 | 1/2011 | Burke et al. |
| 2012/0203273 A1* | 8/2012 | Riskin .................. A61B 17/083 606/213 |
| 2013/0296930 A1* | 11/2013 | Belson .................. A61B 17/08 606/215 |
| 2014/0058444 A1 | 2/2014 | Fox |
| 2016/0114146 A1 | 4/2016 | Belson et al. |
| 2018/0193019 A1* | 7/2018 | Yang .................. A61B 17/085 |
| 2019/0008516 A1 | 1/2019 | Darling, IV |

FOREIGN PATENT DOCUMENTS

| | | |
|---|---|---|
| DE | 2447681 | 4/1976 |
| EP | 0957774 | 11/1999 |
| GB | 1401877 | 8/1975 |
| WO | WO9610954 | 4/1996 |
| WO | WO9629013 | 9/1996 |
| WO | WO9942146 | 8/1999 |
| WO | WO0140348 | 6/2001 |
| WO | WO06026634 | 6/2001 |
| WO | WO2004006782 | 1/2004 |
| WO | WO2006026634 | 3/2006 |
| WO | WO12151366 | 11/2012 |
| WO | WO-2017023901 A1 * | 2/2017 ........... A61B 17/085 |

* cited by examiner

SKIN CLOSURE DEVICES

REFERENCE TO RELATED APPLICATIONS

The present application claims priority to Provisional U.S. Application No. 62/838,623, filed Apr. 25, 2019 and entitled "Pinch-Close Skin Closure Devices," which is incorporated in its entirety.

BACKGROUND

1. Field of the Invention

This invention is directed to devices and methods for closing wounds. Specifically, the invention is directed to devices and methods for closing a wound without stiches, including allowing one handed closure of wounds.

2. Description of the Background

In the closure of wounds, a persistent problem has been having a medium that could reliably close the wound while, at the same, time, being easy to use. Many types of devices are available for such closure. The simplest form has been the skin bandage, sold under various names, such as Band-Aid® of Cur-Aid®. Other adhesives, depending on the type of wound to be closed, have come to market, including forms of adhesive closures such as Steri-Strip® and butterfly bandages. Of course, for simple or complex wounds, there are the traditional methods of wound closure, sutures and staples, supplemented by medical glues for smaller wounds without tension.

However, none of these solutions bring an easy-to-use, flexible approach to wound closure, particularly where the wound is involved that might otherwise require a suture or staple. Either the medium, as normally applied, just holds the wound together or requires a trained medical professional to apply.

In these circumstances, the need for device that can be used as first aid to avoid the possible need for sutures or staples to affect a good closure while allowing for quick, effective and easy-to-use closure of the wound or laceration is apparent. At the same time, such a device has to be able to be easily understood and applied by non-medical people, whether tending to a child or spouse at home or closing up a laceration while engaged in sports or out camping and hiking. In remote areas, and in many situations on the home front, the device often needs to be able to be applied by the injured person because there is no one else readily available to assist in the closure.

SUMMARY

The present invention overcomes the problems and disadvantages associated with current strategies and designs and provides new tools and methods for closing wounds.

One embodiment of is directed to a wound closure device. The wound closure device comprises two clips. Each clip comprising a wedge-shaped body, a tab extending from a tip of the wedge-shaped body, an anchor extending from a base of the wedge-shaped body, and a locking mechanism positioned within the wedge-shaped body. In a preferred embodiment, the two clips are identical. Preferably the wound closure further comprises adhesive coupled to a bottom surface of the anchor and a bottom surface of the wedge-shaped body. The tab from one clip is preferably accepted by the locking mechanism of the second clip. Preferably, the tab extends from a first side of the wedge-shaped body and the locking mechanism is within a second, opposite side of the wedge-shaped body. In a preferred embodiment, the anchor and the tab are not co-planer.

Preferably, the anchor is coupled to the wedge-shaped body by at least one hinge. In a preferred embodiment, the wound closure device is adapted to be closed by one hand. The wound closure device preferably has holes in at least one of the anchor and the wedge shaped body. Preferably, the two clips provide wound eversion when the wound closure device is pinched together.

Another embodiment of the invention is directed to a method of closing a wound with a wound closure device, comprising the steps of: positioning a first clip along one edge of a wound, positioning a second clip along a second side of a wound, and pinching the two clips together to close the wound.

Preferably, each clip comprises a wedge-shaped body, a tab extending from a tip of the wedge-shaped body, an anchor extending from a base of the wedge-shaped body, and a locking mechanism positioned within the wedge-shaped body. In a preferred embodiment, the step of positioning a first clip along one edge of a wound comprises positioned the tip of the wedge-shaped body of the first clip along the edge of the wound and the step of positioning a second clip along one edge of a wound comprises positioned the tip of the wedge-shaped body of the second clip along the edge of the wound. Preferably, the step of pinching the two clips together to close the wound is accomplished with one hand.

In a preferred embodiment, adhesive is coupled to a bottom surface of the anchor and a bottom surface of the wedge-shaped body. The step of positioning a first clip along one edge of a wound preferably comprises affixing the anchor and the wedge-shaped body of the first clip adjacent to one edge of the wound with the adhesive and the step of positioning a second clip along one edge of a wound comprises affixing the anchor and the wedge-shaped body of the second clip adjacent to one edge of the wound with the adhesive. The tab from the first clip is preferably accepted by the locking mechanism of the second clip. Preferably, the anchor and the tab are not co-planer.

Preferably, the two clips are identical. The two clips preferably provide wound eversion when the wound closure device is pinched together. The two clips are preferably two asymmetrical clips. In a preferred embodiment, a first asymmetrical clip comprises a wedge-shaped body, at least one tab extending from a tip of the wedge-shaped body, and an anchor extending from a base of the wedge-shaped body, and a second asymmetrical clip comprises a wedge-shaped body, an anchor extending from a base of the wedge-shaped body, and at least one locking mechanism positioned within the wedge-shaped body. Preferably, each tab of the first asymmetrical clip has a corresponding the locking mechanism in the second asymmetrical clip.

In a preferred embodiment, the step of positioning a first clip along one edge of a wound comprises positioned the tip of the wedge-shaped body of the first clip along the edge of the wound and the step of positioning a second clip along one edge of a wound comprises positioned the tip of the wedge-shaped body of the second clip along the edge of the wound. Preferably, the step of pinching the two clips together to close the wound is accomplished with one hand. Adhesive is preferably coupled to a bottom surface of the anchor and a bottom surface of the wedge-shaped body.

Preferably, the step of positioning a first clip along one edge of a wound comprises affixing the anchor and the wedge-shaped body of the first clip adjacent to one edge of the wound with the adhesive and the step of positioning a second clip along one edge of a wound comprises affixing the anchor and the wedge-shaped body of the second clip adjacent to one edge of the wound with the adhesive. Preferably, the tab from the first clip is accepted by the locking mechanism of the second clip. The anchor and the tab are preferably not co-planer.

Another embodiment of the invention is directed to a wound closure device. The wound closure device comprises two asymmetrical clips, a first asymmetrical clip comprising a wedge-shaped body, at least one tab extending from a tip of the wedge-shaped body, and an anchor extending from a base of the wedge-shaped body, and a second asymmetrical clip comprising a wedge-shaped body, an anchor extending from a base of the wedge-shaped body, and at least one locking mechanism positioned within the wedge-shaped body. Preferably, each tab of the first asymmetrical clip has a corresponding the locking mechanism in the second asymmetrical clip.

In a preferred embodiment, the second asymmetrical clip has at least one tab extending from a tip of the wedge-shaped body and the first asymmetrical clip has at least one locking mechanism positioned within the wedge-shaped body, wherein each tab of the second asymmetrical clip has a corresponding the locking mechanism in the first asymmetrical clip. Preferably, a number of tabs and locking mechanisms in each clip are different than a number of tabs and locking mechanisms in the other clip. The wound closure device preferably further comprises adhesive coupled to a bottom surface of the anchor and a bottom surface of the wedge-shaped body.

Preferably, the tab from the first asymmetrical clip is accepted by the locking mechanism of the second asymmetrical clip. Preferably, the anchor and the tab are not co-planer. In a preferred embodiment, the anchor is coupled to the wedge-shaped body by at least one hinge. Preferably, the wound closure device is adapted to be closed by one hand. The wound closure device preferably further comprises holes in at least one of the anchor and the wedge shaped body. Preferably, the two clips provide wound eversion when the wound closure device is pinched together.

Another embodiment of the invention is directed to a wound closure device composed as one piece. The wound closure device comprises two halves coupled with a hinge. The wound closure device has a first half having a first portion of a coupling mechanism and a second half having a second portion of a coupling mechanism. Preferably, the two halves can be secured together one-handedly, to close and evert a wound.

Preferably, the first portion of the coupling mechanism is an arm and the second portion of the coupling mechanism is a locking mechanism. In a preferred embodiment, the device is a single unit with a single hinge located at a center point of the two halves which extends from the center point. Preferably, the locking mechanism is located in a center housing on the second half with the arm extending from a center housing of the first half. Preferably, the act of closing the device everts the skin. A point of connection between each of the two halves with the center housing for the locking mechanism preferably has a hinge that allows the center housing to flex upon closing. The wound closure device preferably has holes in the device to promote skin breathing.

Other embodiments and advantages of the invention are set forth in part in the description, which follows, and in part, may be obvious from this description, or may be learned from the practice of the invention.

DESCRIPTION OF THE INVENTION

As embodied and broadly described herein, the present invention is directed to devices and methods of closing wounds. The preferred embodiment of the invention is a pinch closure device capable of bilateral closure. In this manner, unlike most other closure systems excepting sutures, both sides of the wound are moved together at the same time. This avoids separation of the layers of the dermis, creating voids that can cause blistering. The device should approximate the wound edges when applied and maintain wound approximation during closure. It should have a clearly defined stopping point to assure that the closure device cannot be overtightened, which in turn can also cause blistering. The device should be able to evert the approximated skin edges during closure so as to assist in cosmesis, hemostasis and restoring blood flow quickly to the wound site.

Preferably the device disclosed herein has the ability to be easily applied by an injured person with no medical or first aid training. Preferably, the device has definite stops on the closure so that the wound cannot be overtightened, a problem even with such traditional closure systems as sutures and even for trained medical professionals. The device preferably maintains approximation of the wound's edges upon closure. Preferably, the device creates eversion of the skin at full closure. The device is preferably a bilateral closure and can be applied with one hand.

Figure 1:
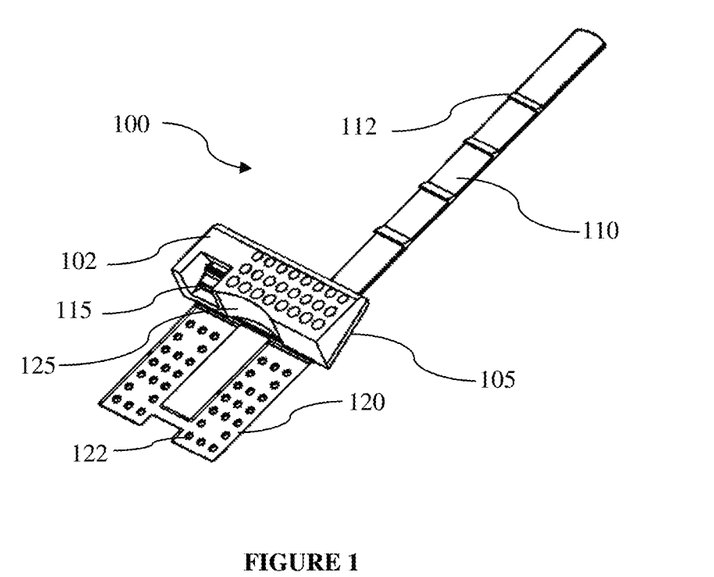
FIG. 1 An isometric view of an embodiment of a clip of the invention.
Figure 2:
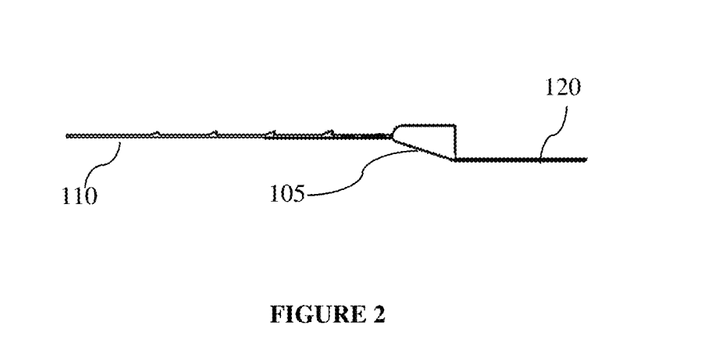
FIG. 2 A side view of the embodiment of a clip of the invention of FIG. 1.

The device is preferably comprised of two clip pieces, or a single clip that can be closed single-handedly. FIG. 1 depicts a perspective view of an embodiment of one of the two clips 100. The two clip pieces may or may not be identical. Each clip piece will be made of a durable material, whether the material be of a metal, plastic, nylon, carbon-fiber, or any other of the numerous durable materials, either singly or in combination with others, that could be utilized to make the piece. Each clip 100 preferably has a body 102 having a wedge or base 105 on the forward edge of body 102 that serves as the pushing mechanism. Body 102 may have an extended tab 110 protruding from the lip of wedge 105 on one side and a receiving entry point or locking mechanism 115 on the other side (see FIG. 3). Tab 110 preferably has teeth 112, as many as needed, but generally thought to be at least one tooth, and as many as (but not by way of limitation) 50 teeth, to allow the locking of the device closed.

Figure 8A:
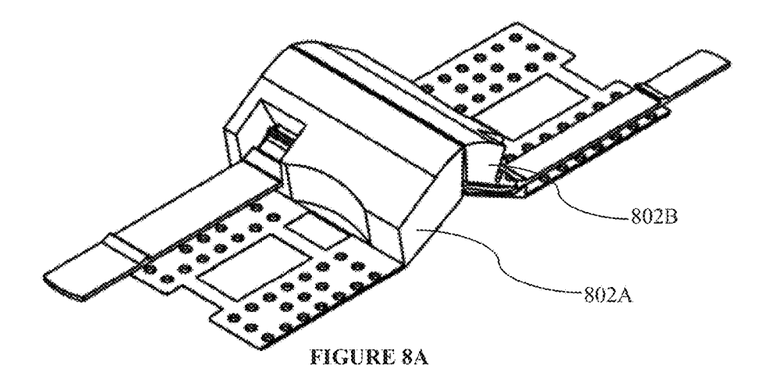
FIGS. 8A-B Views of two coupled clips of a forth embodiment of the invention.
Figure 8B:
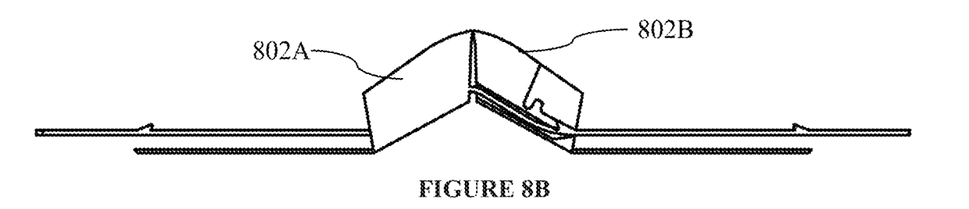
Figure 9A:
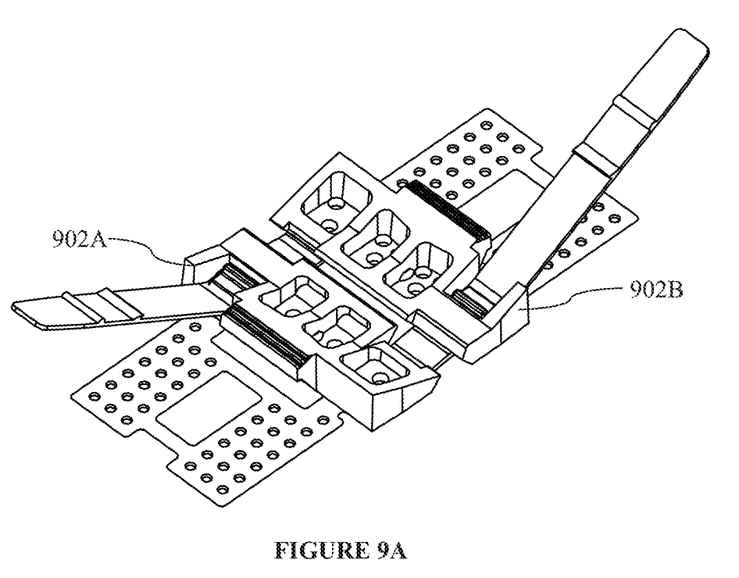
FIGS. 9A-C Views of two coupled clips of a fifth embodiment of the invention.
Figure 9B:
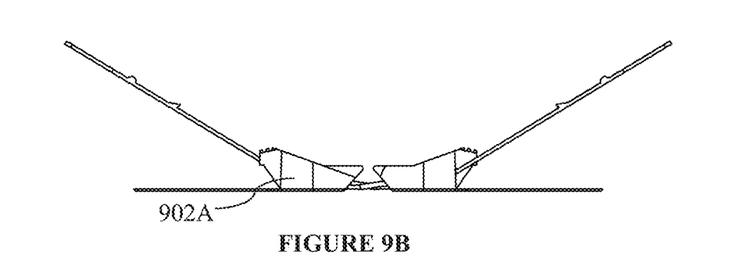
Figure 9C:
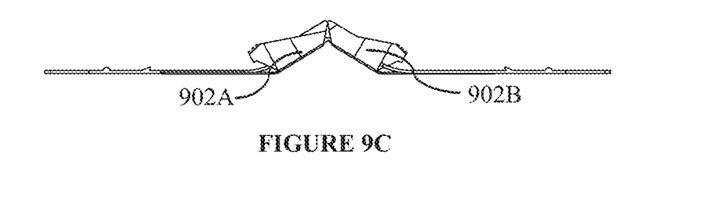

In another embodiment, as shown in FIGS. 8A and 8B, body 802A and 802B the device may have another shape, such as a parallelogram. Preferably, the shape of body 802A and 802B provides the same eversion effect that the embodiment shown in FIGS. 1-5B. As can be seen by comparing FIG. 5A to FIG. 8B, both embodiments preferably come together similarly and provide the similar forces on the wound. The point of connection between the anchors and bodies 802A and B may be hinged or unhinged. FIGS. 9A-C display another embodiment of a wound closing device. Preferably, the shape of body 902A and 902B provides the same eversion effect (shown in FIG. 9C) of the other embodiments described herein. The embodiment shown in FIGS. 9A-C preferably has the same features and functionality as the other embodiments described herein. FIGS. 9A-B show the closing device pre-securement and FIG. 9C shows the closing device after securement with the eversion.

Figure 3:
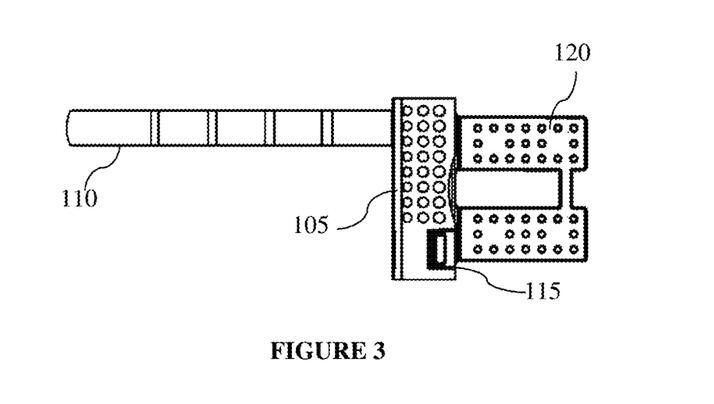
FIG. 3 A top view of the embodiment of a clip of the invention of FIG. 1.
Figure 4:
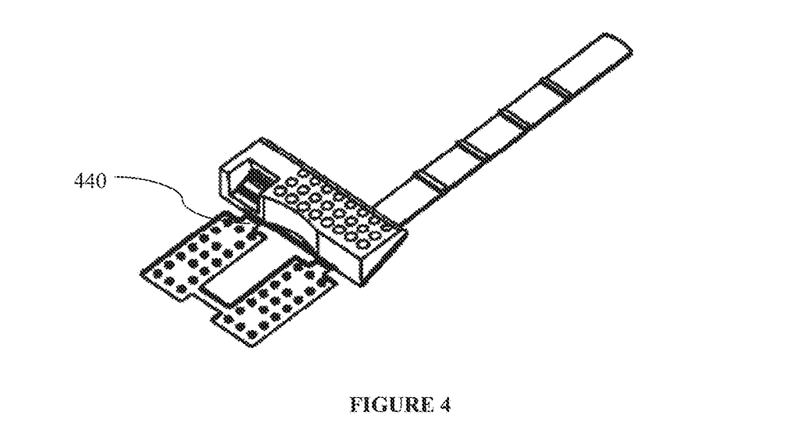
FIG. 4 An isometric view of an embodiment of a clip of the invention with a hinge.

The receiving entry or locking mechanism 115 preferably contains a locking mechanism to allow the device to be securely closed and locked into place. The locking mechanism preferably engages teeth 112 on tab 110. For example, the locking mechanism may allow teeth 112 to enter receiving entry or locking mechanism 115 but not be withdrawn from receiving entry or locking mechanism 115. In addition, there may or may not be a release mechanism to allow the device to be adjusted after initial closure.

In this embodiment, the clips are preferably identical, and the closing of the device is achieved by putting the two clips into a position opposing each other so that the tab 110 on one enters the receiving entry or locking mechanism 115 on the other. Each clip 100 may have a finger hold 125 to provide a surface to push against when closing the device.

The underside of wedge 105 preferably has a rising angle so that looked at from the side (see FIG. 2), it appears to be diagonal, being thick at the beginning of the wedge and thinning as it approaches the point of juncture between the approximated edges of the skin. In some iterations, there may be a lip at the forward edge. The wedge is joined to an anchoring piece 120. The anchoring piece 120, depending upon the material used an its flexibility, may have one or more "live hinges" 440 or narrowed point(s) of connection between the anchor and the wedge (see FIG. 4). In other iterations, the anchoring piece can be directly connected to the wedge with no intervening "hinge," as shown in FIG. 1.

Anchor 120 may or may not have holes 122 drilled, punched, or otherwise manufactured therein, as may wedge 105. Holes 122 preferably allow the wound and surrounding skin to breathe after placement of the device. Holes 122 may prevent the skin under clip 100 from becoming irritated. Additionally, holes 122 may improve the manufacturing process by allowing clip 100 to cool more uniformly and avoid warpage.

Figure 6:
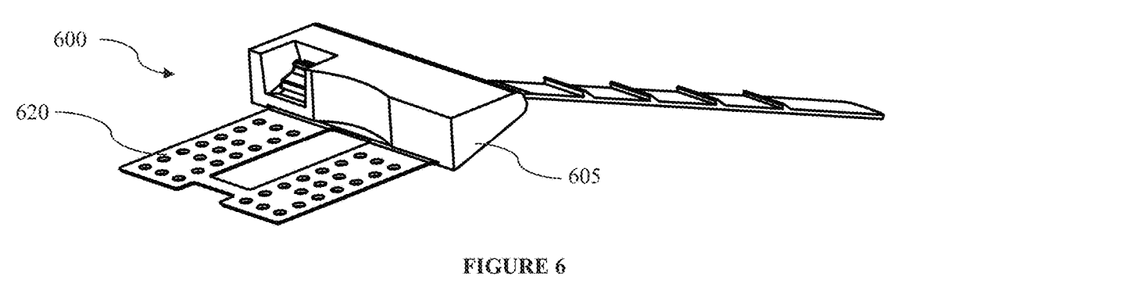
FIG. 6 An isometric view of a second embodiment of a clip of the invention.
Figure 7:
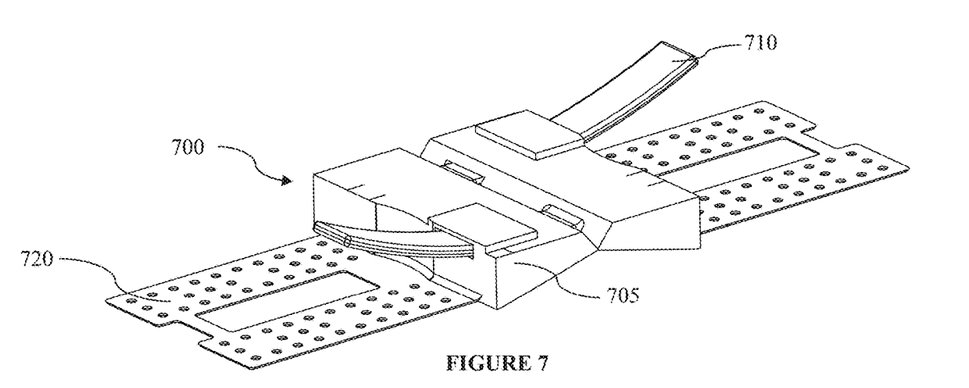
FIG. 7 An isometric view of a third embodiment of two attached clips of the invention.

In the preferred embodiment, anchor 120 is coupled to the bottom of wedge 105, while tab 110 is coupled to the tip of wedge 105. Thus, anchor 120 and tab 110 are parallel to each other but are not co-planer. Preferably, anchor 120 is positioned such that anchor 120 can be placed upon the skin, while tab 110 is positioned such that tab 110 is above the skin. In another embodiment, shown in FIG. 6, clip 600 preferably has tab 610 that may extend at a downward angle from wedge 605. In clip 600, tab 610 and anchor 620 are not parallel. FIG. 7 shows another embodiment of clip 700. In clip 700, tab 710 preferably extends at a curved upward angle from wedge 705. In clip 700, tab 710 and anchor 720 are not parallel. Preferably the curved shape of tab 710 provides greater eversion of the wound edges as the two clips come together.

Clip 100 is preferably secured to the skin with an adhesive coating. This coating may be a medically appropriate adhesive directly applied to the underside of clip 100. Or the adhesive may be on an adhesive carrier in the form of a tape to which clip 100 is attached. Preferably, the adhesive extends along the bottom of anchor 120 and along the angled portion of wedge 105 such that the end of anchor 120 through the tip of wedge 105 maintains contact with the skin upon placement adjacent to the wound. Other forms for attaching the device to the skin may be devised, but this will not affect the intended functioning of the device.

In some variation of clip 100, there will be a top adhesive coating over the top of the device, particularly if an adhesive on an adhesive carrier is utilized to apply the device to the skin. This top adhesive coating can enhance the stability of the closure by helping to assure that clip 100 will not separate from the adhesive securing clip 100 to the skin and closing the wound, since separation may cause wound separation as well. This top adhesive coating may be coated with a protective covering such as a polyurethane coating often used in skin closure in the medical device industry to avoid intrusion of moisture and dirt.

Clip 100 preferably allows eversion of the skin even if no hinging action is built in or observed. Clip 100, surprisingly, creates eversion simply though design. No other design has been discovered that has had embedded in it such an everting function simply tied to a one-piece, non-hinged design. Adding a hinging mechanism may accentuate the everting effect, but the hinging embodiment is not required to create skin eversion. Including a "lifting lip" at end can also provide additional eversion, but such a lip is not required.

For a non-medical professional to single-handedly effect a wound closure has significant positive benefits. Eversion has long been recognized as the "gold standard of wound closure." This arises because eversion avoids inversion of the wound, which creates the potential for significant scarring. In addition, with eversion, live tissue of the wound's edges are put into contact with each other, allowing the body's natural defenses at the wound site to more fully come into play, increasing the potential for better healing and helping to reduce the potential for site infection. The ability of clip 100 create eversion thus gives an ability to non-medical personal to get good closure results in those instances in which a doctor's intervention would not otherwise be required or available from a medical treatment perspective.

Figure 5A:
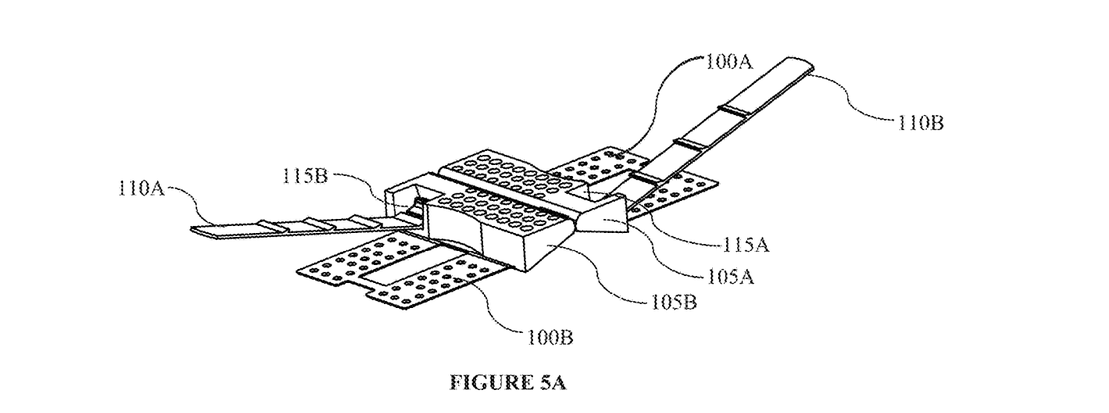
FIGS. 5A-B Views of two coupled clips of the embodiment of FIG. 1.
Figure 5B:
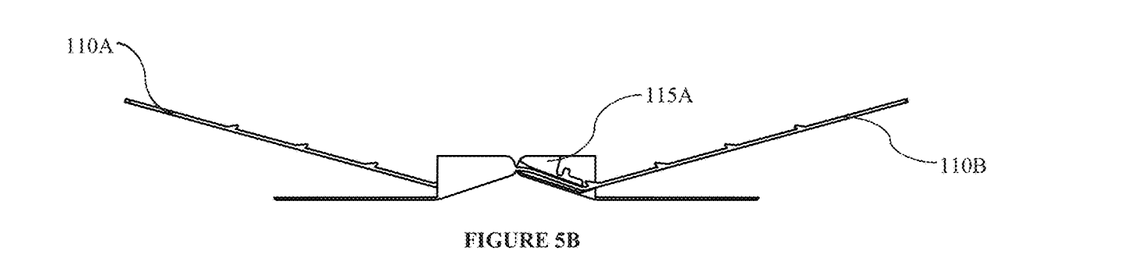

As shown in FIGS. 5A and 5B, when two clips 100A and 100B are brought together, the tab 110A or 110B of each clip 100A or 100B enters the receiving entry or locking mechanism 115B or 115A on the other clip. FIG. 5B depicts the path of tab 110B through locking mechanism 115A.

In use, clips 100A and 100B are brought together until the front edges of wedges 105A and 105B abut and, thereafter, clips 100A and 100B cannot be pushed together any further, thereby limiting the force applied to the wound. Preferably, clips 100A and 100B are pre-assembled and can be applied directly to a wound. However, in other embodiments, clips 100A and 100B must be coupled together prior to application to a wound. Each clip 100 is preferably positioned such that the edge of wedge 105 abuts an edge of the wound. Preferably, anchor 120 and the bottom surface of wedge 105 are secured to the skin with adhesive or another securement method. Once clips 100A and 100B are secured about the wound, clips 100A and 100B are preferably pinched together to bring the edges of wedges 105A and 105B into contact, thereby closing and everting the wound. The pinching can be accomplished with one or two hands.

Figure 10A:
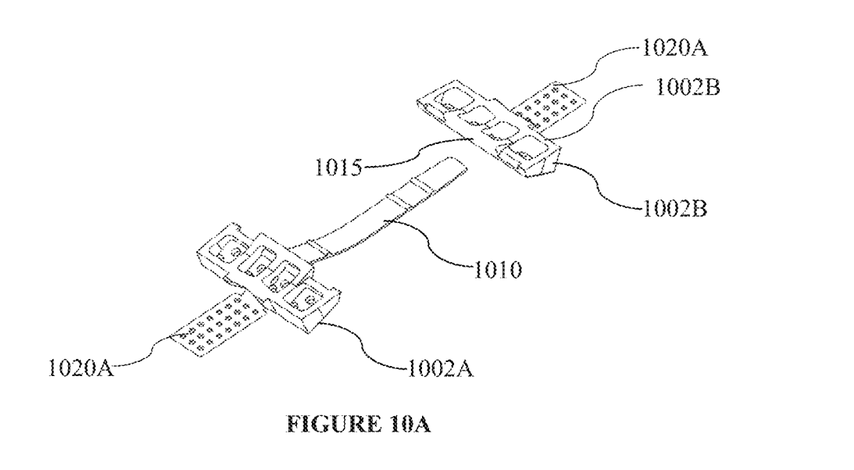
FIGS. 10A-B Views of a first asymmetrical embodiment of the invention.
Figure 10B:
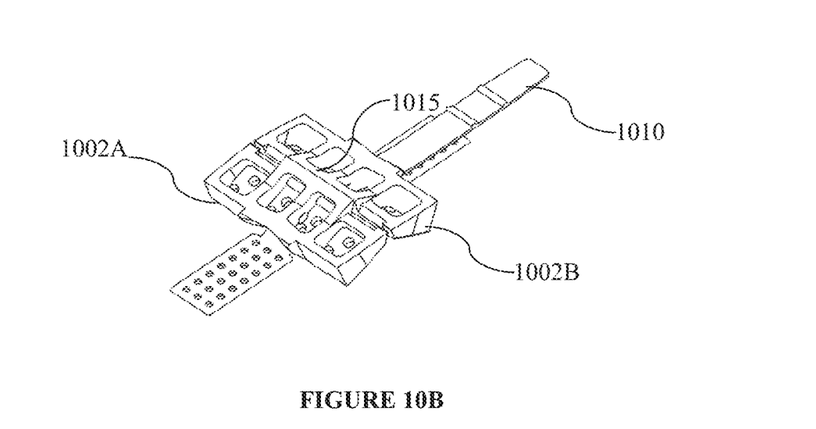

FIGS. 10A-B display an embodiment of an asymmetrical wound closing device. The asymmetrical wound closing device has a first body 1002A with pull tab 1010 and a second body 1002B with entry or locking mechanism 1015 and no pull tab. Preferably, the asymmetrical wound closing device has the same features and functionality as the other embodiments described herein. FIG. 10A show the asymmetrical wound closing device pre-engagement and FIG. 10B shows the asymmetrical wound closing device after securement with the eversion. Preferably each body has an anchor 1020A and 1020B adapted to be coupled to a patient's skin.

Figure 11A:
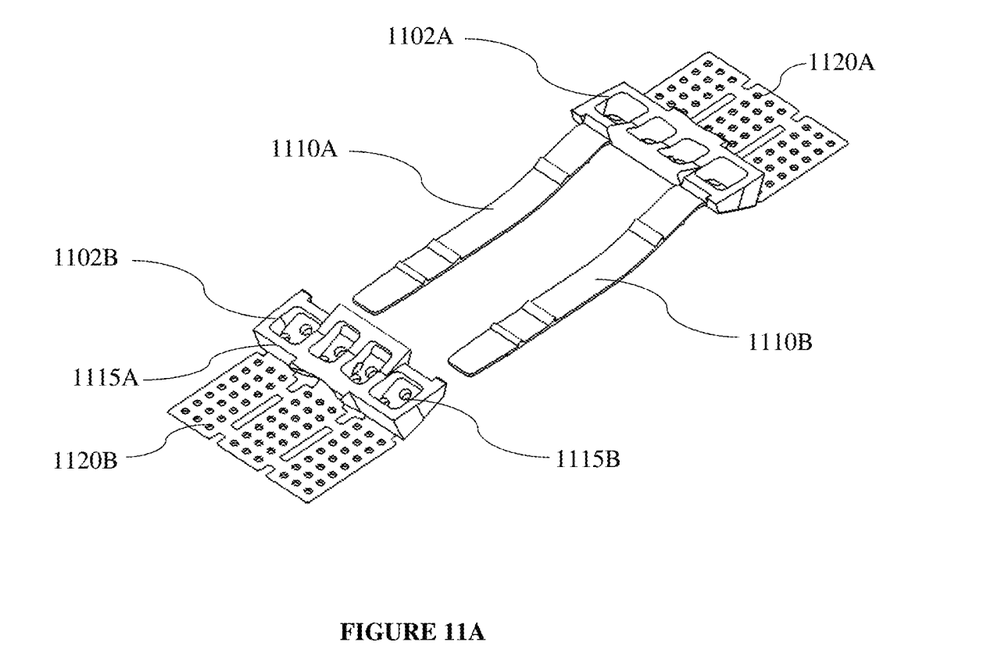
FIGS. 11A-B Views of a second asymmetrical embodiment of the invention.
Figure 11B:
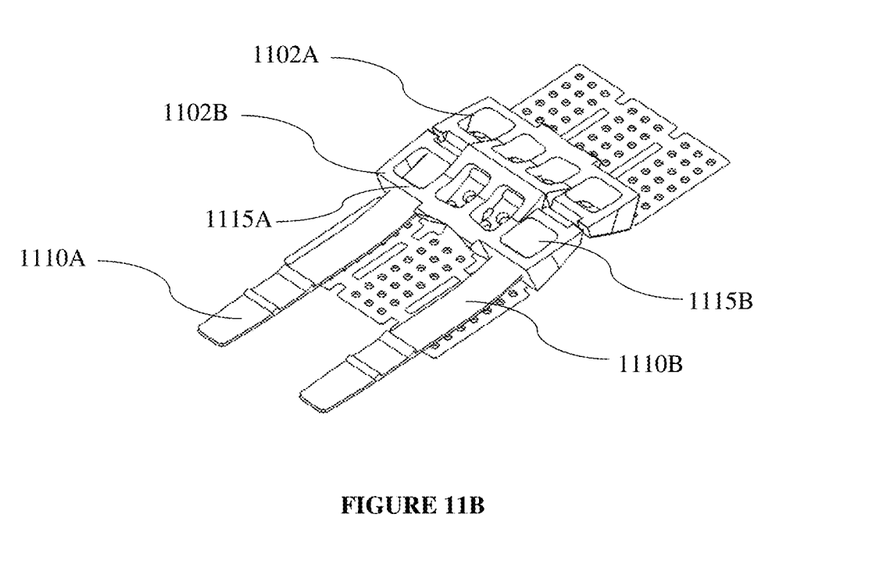

FIGS. 11A and 11B show a second embodiment of an asymmetrical wound closing device. The asymmetrical wound closing device has a first body 1102A with two pull tabs 1110A and 1110B and a second body 1102B with two entry or locking mechanisms 1115A and 1115B and no pull tab. Preferably, the asymmetrical wound closing device has the same features and functionality as the other embodiments described herein. FIG. 11A show the asymmetrical wound closing device pre-engagement and FIG. 11B shows the asymmetrical wound closing device after securement with the eversion. Preferably each body has an anchor 1120A and 1120B adapted to be coupled to a patient's skin.

Figure 12A:
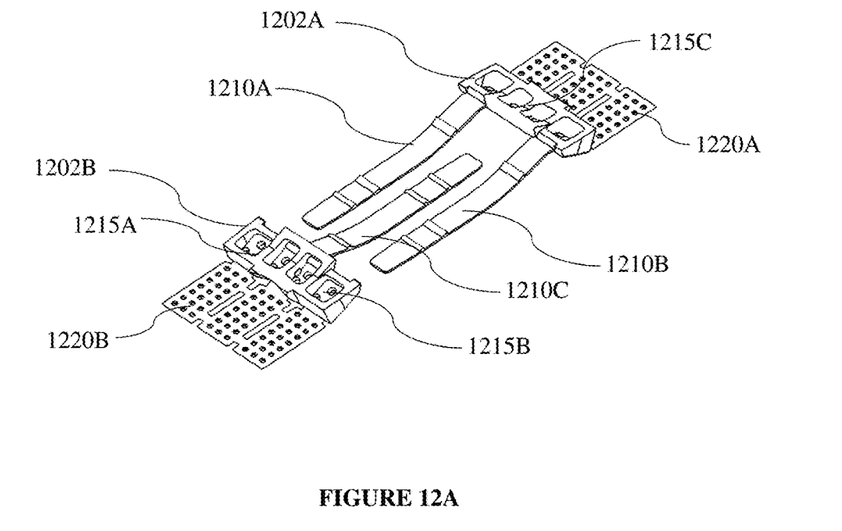
FIGS. 12A-B Views of a third asymmetrical embodiment of the invention.
Figure 12B:
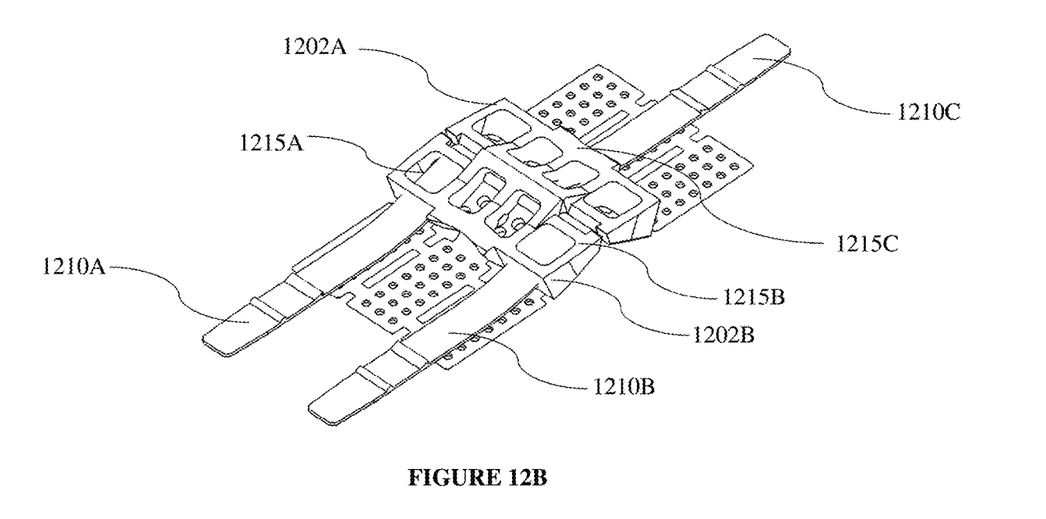

FIGS. 12A and 12B show a third embodiment of an asymmetrical wound closing device. The asymmetrical wound closing device has a first body 1202A with two pull tabs 1210A and 1210B and one entry or locking mechanism 1215C and a second body 1202B with two entry or locking mechanisms 1215A and 1215B and one pull tab 1210C. Preferably, the asymmetrical wound closing device has the same features and functionality as the other embodiments described herein. FIG. 12A show the asymmetrical wound closing device pre-engagement and FIG. 12B shows the asymmetrical wound closing device after securement with the eversion, although the tabs may address to the main part of the device by other manners, as in the manner of the tab in FIG. 2. Preferably each body has an anchor 1220A and 1220B adapted to be coupled to a patient's skin.

While 0, 1, and 2 pull tabs are shown in the asymmetrical embodiments, they may have 3, 4, or more pull tabs. Preferably for each pull tab there is a corresponding entry or locking mechanism. However, there may be more entry or locking mechanism than corresponding pull tabs. For example body 1102A of FIGS. 11A-B and body 1202A of FIGS. 12A-B may be identical with the entry or locking mechanism 1215C only being used if the corresponding body has a pull tab.

Figure 13A:
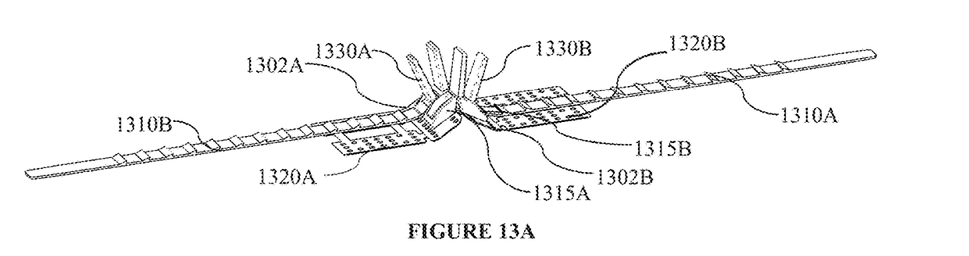
FIGS. 13A-D Views of a releasable embodiment of the invention.
Figure 13B:
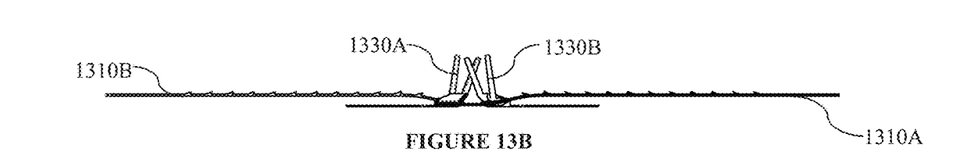
Figure 13C:
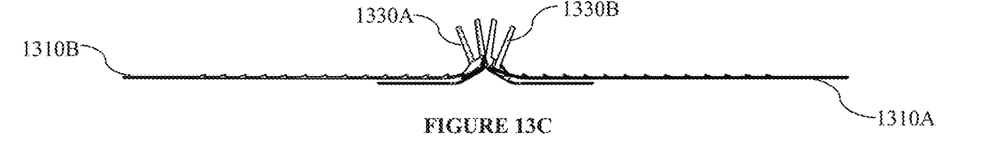
Figure 13D:
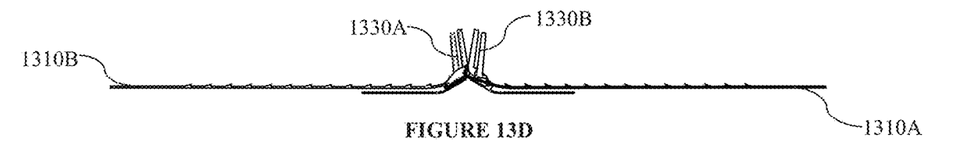

FIGS. 13A-D display an embodiment of a releasable wound closing device. The releasable is preferably comprised of two symmetrical bodies 1302A and 1302B. bodies 1302A and 1302B are similar to the other embodiments described herein with the addition of release tines 1330A and 1330B. Preferably, release tines 1330A-B allow tabs 1310A-B to be released and/or removed from the opposing locking mechanism 1315A-B. For example, as each of tines 1330A and 1330B are pinched or brought together (as shown in FIG. 11D), tabs 1310A-B are able to slide freely within the opposing locking mechanism 1315A-B. However, when tines 1330A and 1330B are released (as shown in FIG. 13C), tabs 1310A-B are locked within the opposing locking mechanism 1315A-B. Preferably each body has an anchor 1320A and 1320B adapted to be coupled to a patient's skin.

Tines 1330A and 1330B may be used to adjust how closely together bodies 1302A and 1302B are positioned around a wound. For example, bodies 1302A and 1302B can be pulled together gradually to facilitate wound closure. Once bodies 1302A and 1302B are fully engaged, tines 1330A and 1330B may be removable. For example, tines 1330A and 1330B may break off or be cut off, thereby preventing a patient from inadvertently releasing the device.

Another embodiment of the device preferably includes a single clip joined together at the wedge, either in total fashion, at the edges, or in the center, where the joint has a lever mechanism that allows the device to be closed by pushing on the wedges, which is turn cause the lever mechanism at the top of the device to bring the device together.

FIGS. 14A-D show an embodiment of a single unit embodiment of a wound closing device 1400. Wound closing device 1400 is preferably comprised of two halves 1402A and 1402B coupled together with a hinge 1414. Halves 1402A and 1402B may be symmetrical, as shown in the figures, or asymmetrical as described herein with regard to the other embodiments. Hinge 1414 is preferably a living hinge made of a flexible strip of material between halves 1402A and 1402B. However, hinge 1414 may be another device capable of allowing halves 1402A and 1402B to move relative to each other to evert a wound.

Preferably, at least one of halves 1402A and 1402B has one or more pull tabs 1410A-B extending from the associated half toward the other half. Preferably, for each pull tab 1410A-B, there is a corresponding locking mechanism 1415A-B in the other half which is adapted to receive the pull tab 1410A-B. In other embodiments, a different coupling mechanism may be used. For example the coupling mechanism may be a hook and loop closure, snaps, adhesive, magnets, latches, or another device capable of holding the halves together upon contact. Preferably each half has an anchor 1420A and 1420B adapted to be coupled to a patient's skin.

Figure 14A:
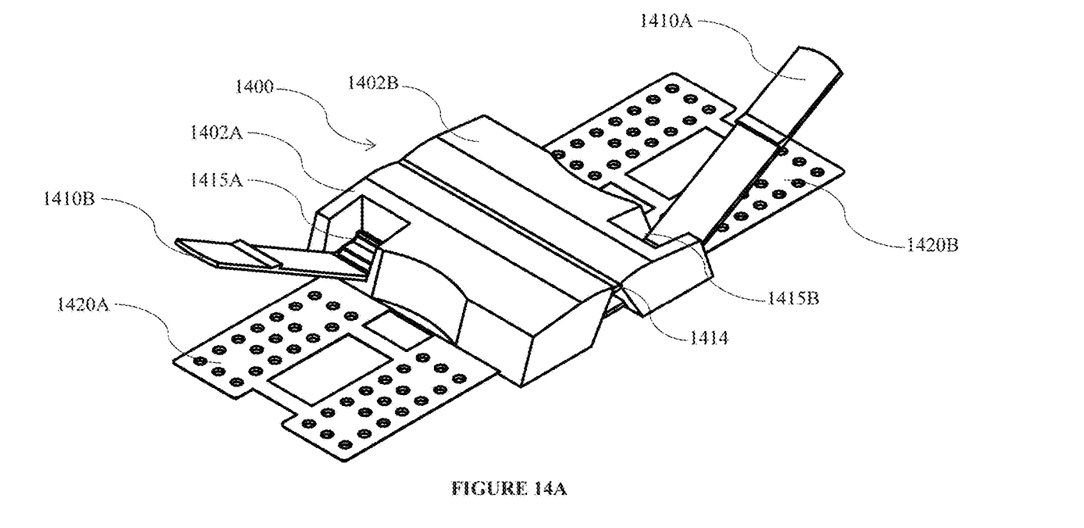
FIGS. 14A-D Views of a single unit embodiment of the invention.
Figure 14B:
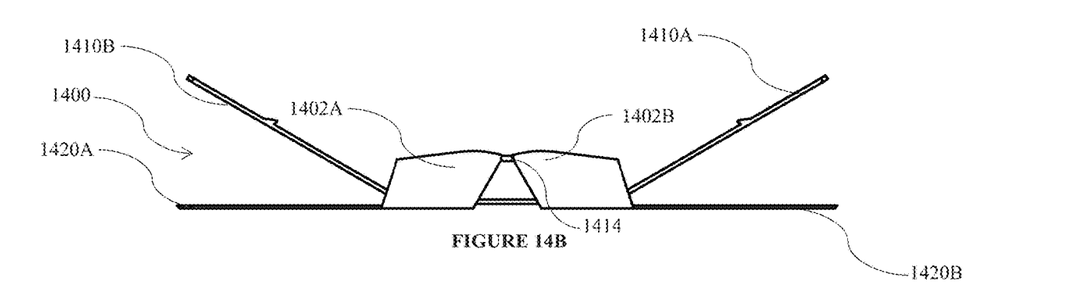
Figure 14C:
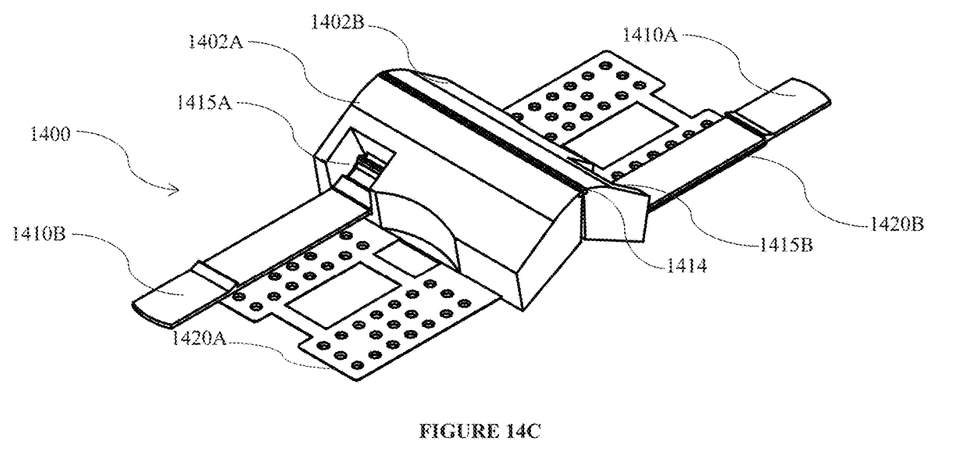
Figure 14D:
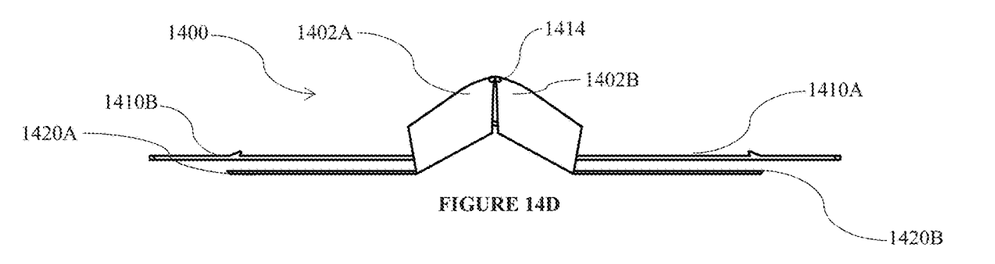

Preferably, FIGS. 14A-B show wound closing device 1400 in an open state. In the open state, halves 1402A and 1402B are able to be placed about a wound. Preferably, FIGS. 14C-D show wound closing device 1400 in a closed state. In the closed state, pull tabs 1410A-B are pulled through locking mechanisms 1415A-B, thereby forcing halves 1402A and 1402B to rotate about hinge 1414 and pull the wound together and evert the wound edge. The point of connection between the anchors 1420A and 1420B and halves 1402A and B may be hinged or unhinged.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A wound closure device, comprising:
   two clips, each clip comprising:
   a wedge-shaped body having a first thick end tapering to a second narrow end;
   a tab extending from the narrow end of the wedge-shaped body;
   an anchor extending from an edge of the thick end of the wedge-shaped body; and
   a lock positioned within the wedge-shaped body;
   wherein the two clips provide wound eversion when the wound closure device is pinched together.

2. The wound closure device of claim 1, wherein the two clips are identical.

3. The wound closure device of claim 1, further comprising adhesive coupled to a bottom surface of the anchor and a bottom surface of the wedge-shaped body of each of the two clips.

4. The wound closure device of claim 1, wherein the tab from one clip of the two clips is accepted by a lock of the second clip of the two clips.

5. The wound closure device of claim 1, wherein, for each of the two clips, the tab extends from a first side of the wedge-shaped body and the lock is within a second, opposite side of the wedge-shaped body.

6. The wound closure device of claim 1, wherein, for each of the two clips, the anchor and the tab are not co-planer.

7. The wound closure device of claim 1, wherein, for each of the two clips, the anchor is coupled to the wedge-shaped body by at least one hinge.

8. The wound closure device of claim 1, wherein the wound closure device is adapted to be closed by one hand.

9. The wound closure device of claim 1, further comprising, in each of the two clips, holes in at least one of the anchor and the wedge shaped body.

10. A method of closing a wound with the wound closure device of claim 1, comprising the steps of:
    positioning a first clip of the two clips along one edge of a wound;
    positioning a second clip of the two clips along a second edge of the wound; and
    pinching the two clips together to close the wound.

11. The method of claim 10, wherein the step of positioning the first clip of the two clips along the one edge of a wound comprises positioning the second narrow end of the wedge-shaped body of the first clip along the one edge of the wound and the step of positioning the second clip of the two clips along the second edge of a wound comprises positioning the second narrow end of the wedge-shaped body of the second clip along the second edge of the wound.

12. The method of claim 10, wherein the step of pinching the two clips together to close the wound is accomplished with one hand.

13. The method of claim 10, further comprising coupling adhesive to a bottom surface of the anchor and a bottom surface of the wedge-shaped body of each of the two clips.

14. The method of claim 13, wherein the step of positioning the first clip along one edge of a wound comprises affixing the anchor and the wedge-shaped body of the first clip adjacent to the one edge of the wound with the adhesive and the step of positioning the second clip along the second edge of a wound comprises affixing the anchor and the wedge-shaped body of the second clip adjacent to the second edge of the wound with the adhesive.

15. The method of claim 10, wherein the tab from the first clip is accepted by the lock of the second clip and the tab from the second clip is accepted by the lock of the first clip.

16. The method of claim 10, wherein the anchor and the tab of the two clips are not co-planer.

17. The method of claim 10, wherein the two clips are identical.

* * * * *